(12) United States Patent
Polak et al.

(10) Patent No.: US 8,354,452 B2
(45) Date of Patent: Jan. 15, 2013

(54) COMPOSITIONS AND METHODS FOR TREATING DIABETES AND NEUROPSYCHOLOGICAL DYSFUNCTION

(75) Inventors: Michel Polak, Paris (FR); Paul Czernichow, Paris (FR)

(73) Assignees: Assistance Publique-Hopitaux de Paris, Paris (FR); Universite Paris Descartes, Paris Cedex (FR)

( * ) Notice: Subject to any disclaimer, the term of this patent is extended or adjusted under 35 U.S.C. 154(b) by 676 days.

(21) Appl. No.: 12/373,982

(22) PCT Filed: Aug. 1, 2007

(86) PCT No.: PCT/EP2007/057937
§ 371 (c)(1),
(2), (4) Date: Jan. 15, 2009

(87) PCT Pub. No.: WO2008/015226
PCT Pub. Date: Feb. 7, 2008

(65) Prior Publication Data
US 2009/0306212 A1  Dec. 10, 2009

(30) Foreign Application Priority Data
Aug. 2, 2006 (EP) ..................... 06291256

(51) Int. Cl.
*A61K 31/16* (2006.01)
*A61K 31/12* (2006.01)
(52) U.S. Cl. .......................... 514/616; 514/579; 514/675
(58) Field of Classification Search ........................ None
See application file for complete search history.

(56) References Cited

FOREIGN PATENT DOCUMENTS
EP     1 782 815    5/2007

OTHER PUBLICATIONS

Shyng et al., Functional Analyses of Novel Mutations in the Sulphonylurea Receptor 1 Associated With Persistent Hyperinsulinemic Hypoglycemia of Infancy, Diabetes, vol. 47, Jul. 1998, 1145-1151.*
Yan et al., Sulfonylureas Correct Trafficking Defects of ATP-sensitive Potassium Channels Caused by Mutations in the Sulfonylurea Receptor, J. Biol. Chem., 279 (12): 11096-11105, Mar. 19, 2004.*
Hattersley et al., Activating Mutations in Kir6.2 and Neonatal Diabetes—New Clinical Syndromes, New Scientific Insights, and New Therapy, Diabetes, 54(9) Sep. 2005, pp. 2503-2513.*
Shimomura et al., Mutations at the Same Residue (R50) of Kir6.2 (KCNJ11) That Cause Neonatal Diabetes Produce Different Functional Effects, Diabetes, vol. 55, Jun. 2006, 1705-1712.*
Vila-Carriles et al., FASEB, Jan. 2007, vol. 21: 18-25.*
Babenko, A.P. et al., "Activating mutations in the ABCC8 gene in neonatal diabetes mellitus" *New England Journal of Medicine*, Aug. 2006, pp. 456-466, vol. 355, No. 5.
Hattersley, A.T. et al., "Activating mutations in Kir6.2 and neonatal diabetes—New clinical syndromes, new scientific insights, and new therapy" *Diabetes*, Sep. 2005, pp. 2503-2513, vol. 54, No. 9.
Pearson, E.R. et al., "Switching from insulin to oral sulfonylureas in patients with diabetes due to Kir6.2 mutations" *New England Journal of Medicine*, Aug. 3, 2006, pp. 467-477, vol. 355, No. 5.
Sagen, J.V. et al., "Permanent neonatal diabetes due to mutations in KCNJ11 encoding Kir6.2—Patient characteristics and initial response to sulfonylurea therapy" *Diabetes*, Oct. 2004, pp. 2713-2718, vol. 53, No. 10.
Shimomura, K. et al., "Mutations at the same residue (R50) of Kir6.2 (KCNJ11) that cause neonatal diabetes produce different functional effects" *Diabetes*, Jun. 2006, pp. 1705-1712, vol. 55, No. 6.
Zung, A. et al., "Glibenclamide treatment in permanent neonatal diabetes mellitus due to an activating mutation in Kir6.2" *Journal of Clinical Endocrinology & Metabolism*, Nov. 2004, pp. 5504-5507, vol. 89, No. 11.
Vaxillaire, M. et al. "Activating mutations of the sulfonylurea receptor SUR1/ABCC8 in permanent and transient neonatal diabetes with frequent familial cosegregation of diabetes" *Diabetes & Metabolism*, Mar. 2006, O62, pp. S29-S30, vol. 32, No. Suppl. 1.
Proks, P. et al. "A heterozygous activating mutation in the sulphonylurea receptor SUR1 (ABCC8) causes neonatal diabetes" *Human Molecular Genetics*, 2006, pp. 1793-1800, vol. 15, No. 11.

* cited by examiner

*Primary Examiner* — Sreeni Padmanabhan
*Assistant Examiner* — Svetlana M Ivanova
(74) *Attorney, Agent, or Firm* — Saliwanchik, Lloyd & Eisenschenk (57) ABSTRACT

The present invention relates to compositions and methods for treating diabetes mellitus, neuropsychological and neurological disorders in a particular group of patient. More specifically, the invention relates to methods of treating diabetes mellitus, neuropsychological and neurological disorders in patients having defective potassium channels. The invention may be used in human subjects, particularly adults or children, and is appropriate to treat various neurological disorders.

8 Claims, 4 Drawing Sheets

COMPOSITIONS AND METHODS FOR TREATING DIABETES AND NEUROPSYCHOLOGICAL DYSFUNCTION

CROSS-REFERENCE TO RELATED APPLICATION

This application is the U.S. national stage application of International Patent Application No. PCT/EP2007/057937, filed Aug. 1, 2007, the disclosure of which is hereby incorporated by reference in its entirety, including all figures, tables and amino acid or nucleic acid sequences.

The present invention relates to compositions and methods for treating diabetes mellitus, neuropsychological, muscular and neurological disorders in a particular group of patient. More specifically, the invention relates to methods of treating diabetes mellitus, neuropsychological, muscular and neurological disorders in patients having defective potassium channels. The invention may be used in human subjects, particularly adults or children, and is appropriate to treat various neurological disorders.

INTRODUCTION

ATP-sensitive potassium channels ($K_{ATP}$) couple cell metabolism to electrical activity by regulating potassium movement across the membrane. These channels are octameric complex with two kinds of subunits: four regulatory sulfonylurea receptor (SUR) embracing four pore-forming inwardly rectifying potassium channel (Kir). Several isoforms exist for each type of subunits: SUR1 is found in the pancreatic β-cell and neurons, whereas SUR2A is in heart cells and SUR2B in smooth muscle; Kir6.2 is in the majority of tissues as pancreatic β-cell, brain, heart and skeletal muscle, and Kir6.1 can be found in smooth vascular muscle and astrocytes. The $K_{ATP}$ channels play multiple physiological roles in the glucose metabolism regulation, especially in β-cell where it regulates insulin secretion, in response to increasing in ATP concentration. They also seem to be critical metabolic sensors in protection against metabolic stress as hypo or hyperglycemia, hypoxia, ischemia.

Persistent hyperinsulinemic hypoglycaemia (HI) of infancy is a heterogeneous disorder which may be divided in two forms on the histopathological lesion (diffuse and focal). Different inactivating mutations have been implied in both forms: the permanent inactivation of the $K_{ATP}$ channels provokes inappropriate insulin secretion, despite low ATP. The diazoxide, used efficiently in certain HI, opens the $K_{ATP}$ channels and therefore overpass the mutation effect on the insulin secretion. Conversely, several studies reported sequencing of KCNJ11, coding for Kir6.2, in patients with permanent neonatal diabetes mellitus and found different mutations for 30 to 50% of the cases. Approximately 28 heterozygous activating mutations have now been identified, the most frequent mutation being in the amino acid R201. These mutations result in reduced ATP-sensitivity of the $K_{ATP}$ channels compared with the wild-types and the level of channel block is responsible for different clinical features: the "mild" form confers isolated permanent neonatal diabetes whereas the severe form combines diabetes and neurological symptoms such as epilepsy, developmental delay, muscle weakness and mild dimorphic features. Sulfonylureas close $K_{ATP}$ channels by binding with high affinity to SUR.

SUMMARY OF THE INVENTION

Here, we showed for the first time that sulfonylurea therapy may be used in a group of subjects having a defective, mutated, potassium channel, in particular ATP-sensitive potassium channel. More specifically, the invention showed that sulfonylurea therapy may be used to treat subjects having mutated SUR1 polypeptides, and is able to replace insulin in those diabetic patients.

Surprisingly, we also showed that sulfonylurea therapy may be used in such group of patients for the treatment of neuropsychological, muscular and neurological disorders, including ocular disorders. More specifically, we designed a protocol to transfer and evaluate children who have insulin treated diabetes due to KCNJ11 mutation, from insulin to sulfonylurea. Our results show that the transfer from insulin injections to oral glibenclamide therapy is highly effective for most patients and safe.

Furthermore, we recently screened the 39 exons of ABCC8 in 34 patients diagnosed with permanent or transient neonatal diabetes (ND) of unknown origin in a case series of 73 ND patients. We identified seven missense mutations in nine patients. Four mutations were familial and showed vertical transmission with neonatal and adult-onset diabetes; the remaining mutations were de novo. Despite being the receptor of the sulfonylureas, our results unexpectedly show that treatment with sulfonylureas in patients with mutated SUR1 achieved euglycemia.

This illuminates how the molecular understanding of some monogenic form of diabetes may lead to an unexpected change of the treatment in children. This is a spectacular example by which a pharmacogenomic approach improves in a tremendous way the quality of life of our young patients.

An object of this invention relates to the use of a potassium channel ligand for the preparation of a pharmaceutical composition for treating diabetes mellitus or/and a neuropsychological, a muscular and a neurological disorder in a subject having a defective, mutated potassium channel (ATP-sensitive $K^+$ channels) subunit.

In a particular aspect of this invention, the invention concerns the use of a potassium channel ligand for the preparation of a pharmaceutical composition for treating diabetes mellitus or/and a neuropsychological, a muscular and a neurological disorder in a subject having a defective, mutated potassium channel SUR1 subunit.

A further object of this invention is a method of treating diabetes mellitus or/and a neuropsychological, a muscular and a neurological disorder in a subject having a defective, mutated potassium channel SUR1 subunit, the method comprising administering to the subject an effective amount of a potassium channel ligand. Preferably, the effective amount is an amount which reduces the channel opening, or closes the channel, preferably for a period of time sufficient to induce or restore membrane depolarization.

A further object of this invention is a method of treating diabetes mellitus or/and a neuropsychological, a muscular and a neurological disorder in a subject, the method comprising a step of determining whether the subject has a defective, mutated potassium channel SUR1 subunit, the presence of such a mutated subunit being an indication that the subject may benefit from a treatment with a potassium channel ligand.

A further object of this invention is a method of determining whether a patient suffering of diabetes mellitus or/and a neuropsychological, a muscular and a neurological disorder may be treated with a potassium channel ligand, the method comprising determining whether the subject has a defective, mutated potassium channel SUR1 subunit.

Preferably, the SUR1 subunit presents an activating mutation increasing the probability of the channel opening, thereby preventing depolarization and limiting insulin secretion. In a preferred embodiment, the mutated SUR1 polypeptide exhibits at least one of the following amino acid mutations: L213R, I1424V, C435R, L582V, H1023Y, R1182Q, and R1379C. Optionally, the potassium channel can also present a mutated Kir6.2 polypeptide. Preferably, the potassium channel does not present a mutated Kir6.2 polypeptide.

In another particular aspect of this invention, the invention concerns the use of a potassium channel ligand for the preparation of a pharmaceutical composition for treating a neuropsychological, a muscular and/or a neurological disorder in a subject. Preferably, the subject has a defective, mutated potassium channel subunit. Preferably, the defective, mutated potassium channel subunit presents an activating mutation increasing the probability of the channel opening, thereby preventing depolarization and limiting insulin secretion. In a particular embodiment, the subject is also suffering of diabetes mellitus. In another embodiment, the subject is not suffering of diabetes mellitus.

In a first embodiment, the subject has a mutated SUR1 polypeptide, preferably exhibiting at least one of the following amino acid mutations: L213R, I1424V, C435R, L582V, H1023Y, R1182Q, and R1379C.

In a second embodiment, the subject has a mutated Kir6.2 polypeptide, preferably exhibiting at least one of the following amino acid mutations: F35V, F35L, H46Y, R50Q, Q52R, G53N, G53R, G53S, V59G, V59M, L164P, K170T, I182V, R201C, R201H, R201 L, I296L, E322K, Y330C, Y330S, and F333I. Preferably, the mutated Kir6.2 polypeptide exhibits at least one of the following amino acid mutations: F35V, F35L, H46Y, R50Q, G53N, G53R, G53S, V59G, V59M, K170T, I182V, R201C, R201H, R201 L, E322K, Y330C, Y330S, and F333I.

A further object of this invention is a method of treating a neuropsychological, a muscular and/or a neurological disorder in a subject, preferably having a defective, mutated potassium channel subunit, the method comprising administering to the subject an effective amount of a potassium channel ligand. Preferably, the effective amount is an amount which reduces the channel opening, or closes the channel, preferably for a period of time sufficient to induce or restore membrane depolarization.

A further object of this invention is a method of treating a neuropsychological, a muscular and/or a neurological disorder in a subject, preferably having a defective, mutated potassium channel subunit, the method comprising a step of determining whether the subject has a defective, mutated potassium channel subunit, the presence of such a mutated subunit being an indication that the subject may benefit from a treatment with a potassium channel ligand. In a particular embodiment, the step of determining whether the subject has a defective, mutated potassium channel subunit comprises the step of determining the presence of a mutated Kir6.2 polypeptide and/or a mutated SUR1 polypeptide. Optionally, the step of determining whether the subject has a defective, mutated potassium channel subunit comprises the step of determining the presence of a mutated Kir6.2 polypeptide and, in absence of a mutated Kir6.2 polypeptide, the step of determining the presence of a mutated SUR1 polypeptide.

A further object of this invention is a method of determining whether a patient suffering of a neuropsychological, a muscular and/or a neurological disorder may be treated with a potassium channel ligand, the method comprising determining whether the subject has a defective, mutated potassium channel subunit. In a particular embodiment, the step of determining whether the subject has a defective, mutated potassium channel subunit comprises the step of determining the presence of a mutated Kir6.2 polypeptide and/or a mutated SUR1 polypeptide. Optionally, the step of determining whether the subject has a defective, mutated potassium channel subunit comprises the step of determining the presence of a mutated Kir6.2 polypeptide and, in absence of a mutated Kir6.2 polypeptide, the step of determining the presence of a mutated SUR 1polypeptide.

A further object of this invention relates to the use of a potassium channel ligand for the preparation of a pharmaceutical composition for treating a neuropsychological, a muscular and/or a neurological disorder.

Preferably, the neuropsychological, muscular and/or neurological disorder is selected from epilepsy, developmental delay, muscle weakness, dyspraxia, dyslexia, dystonia, dysphasia, and ocular disorders including chorioretinal disorders. For instance, chorioretinal disorders can be chorioretinal neovascularizations, retinal edema, permeability disorders and/or ocular degenerative disorders. For the chorioretinal disorders, the ligand can be administered to the subject by oral or intraocular routes. In particular, visiomotor dyspraxia may be improved by the potassium channel ligand. Muscular disorders include neuromuscular disorders, myopathy, Huntington's disease, amyotrophic lateral sclerosis, spinal muscular atrophies (SMA), primary lateral sclerosis (PLS), inherited ataxia, progressive muscular atrophy, postpolio syndrome, and muscular dystrophy, etc.

In particular, the ligand is an ATP-sensitive potassium channel ligand. The potassium channel ligand may be selected e.g. from sulfamides and glinides, either alone or in any combination. In particular, the ligand can be selected among the following drug types: hypoglycemic sulfamide (e.g. carbutamide (Glucidoral), glibenclamide or glyburide (USA) (Daonil, Daonil Faible, Euglucan, Hemi-Daonil, Miglucan), glibornuride (Glutril), glicazide (Diamicron), glimepiride (Amarel), and glipizide (Glibenese, Minidiab, Ozidia)), glinides (e.g. repaglinide (NovoNorm); and associations (e.g. mefformine+glibenclamide (Glucovance). Such ligands include the sufonylureas. A preferred dose is comprised between about 0.05 to about 1.5 mg/kg/day. More preferably, the dose is comprised between about 0.25 to about 1.2 mg/kg/day, still more preferably from 0.30 to 0.8 or 1 mg/kg/day. These does are at the high end of, or exceed, doses recommended by the Food and Drug Administration for treating type 2 diabetes in adults. In addition, the dosage can be decreased after the cessation of insulin. The daily dose is preferably administered in two, three or four times. In a preferred embodiment, the ligand is orally administered.

The subject may be any mammal, preferably a human subject, such as an adult or a child. In a particular embodiment, the subject is a child. In a preferred embodiment, the subject has no detectable anti-islet antibodies, and ultrasonography revealed no pancreatic abnormalities. The present invention may apply also for animals and be used in veterinary medicine, for example for ocular and/or muscular pathologies. Accordingly, the subject can be an animal, preferably a mammal. The subject can be for example a pet animal such as a dog, a cat or a horse, or a farm animal such as a cow, a pig, a sheep, and a goat.

A particular object of this invention relates to the use of a sulfamide or glinide compound for the preparation of a pharmaceutical composition for treating diabetes mellitus or/and a neuropsychological and/or a muscular and/or a neurological disorder (including an ocular one) is a subject, preferably a child, having a SUR1 mutated polypeptide.

The invention also relates to a method of treating diabetes mellitus or/and a neuropsychological and/or a muscular and/or a neurological disorder (including an ocular one) in a subject, preferably a child, having a mutated SUR1 polypeptide, the method comprising administering to the children an effective amount of a sulfamide or glinide.

The SUR1 protein is the sulfonylurea receptor encoding by the gene ABCC8 (UniGene Hs.54470; Genbank NP_000343 and NM_000352). Therefore, the possibility that the mutation altered the binding and that no sulfonylurea binding could be present in the patient was considered. However and despite this theoretical possibility, following identification of their mutations, glibenclamide (glyburide) therapy was initiated and unexpectedly found to be successful in the human PND (permanent neonatal diabetes) patients: insulin was discontinued after 2 and 15 days in patients PND12 and 16, respectively. The current doses of glibenclamide (glyburide) are 0.59 and 0.22 mg/kg/day in patients PND12 and PND16, respectively. These results are unexpected and demonstrate, in human subjects, the efficacy of the present invention.

LEGEND TO THE FIGURES

FIG. 1. Different $K_{ATP}$ channel forms and metabolic regulation. Several isoforms of either Kir and SUR subunits are found in the different organs and confer to the channels their specificity but all interfere with the glucose metabolism. The channels Kir6.2/SUR1 are found in neurons and pancreas, whereas the Kir6.2/SUR2 are found in heart and skeletal muscle.

DETAILED DESCRIPTION OF THE INVENTION

Introduction

ATP-sensitive potassium channels ($K_{ATP}$) are ubiquitous channels coupling cell metabolism to electrical activity by regulating the potassium movements across the cell membrane. Numerous physiological studies of these channels permitted to understand their essential role in many organs, and especially in the glucose metabolism. These channels are composed of 2 types of subunits: the pore-forming subunits Kir embraced by the regulating subunits SUR. Several isoforms of these channels exist in different cellular types. The understanding of their role in the insulin secretion in the pancreatic beta cell has permitted to identify numerous mutations responsible for persistent hyperinsulinism or neonatal diabetes mellitus, and therefore change the therapeutic issue of these patients.

Physiology of the Potassium Channel

Figure 1:
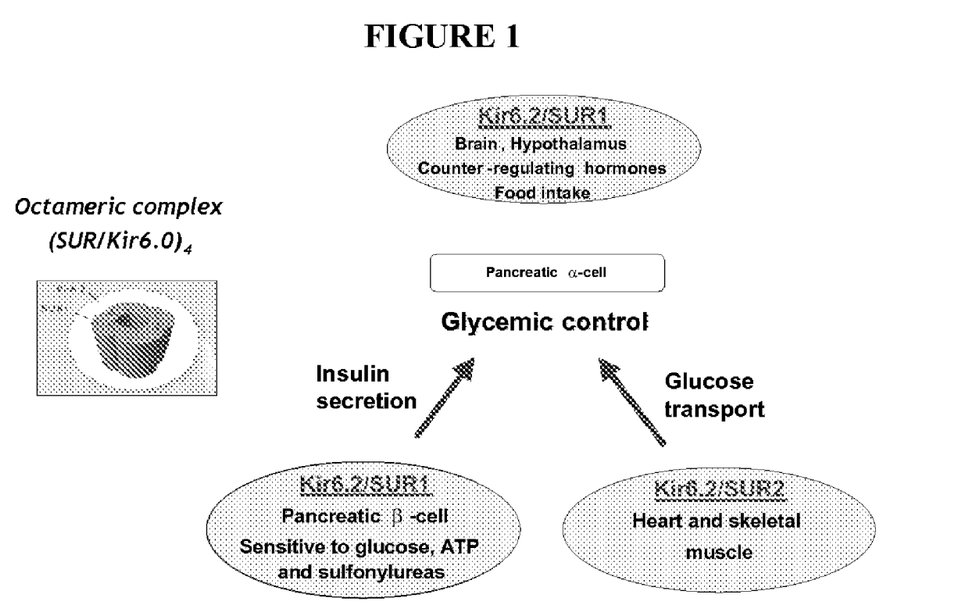

ATP-sensitive potassium channels ($K_{ATP}$) couple cell metabolism to electrical activity by regulating potassium movement across the membrane. These channels are octameric complex with two kind of subunits: four regulatory sulfonylurea receptor (SUR) embracing four poreforming inwardly rectifying potassium channel (Kir) [1, 2]. A 1:1 SUR1: KIR6.2 stochiometry is both necessary and sufficient for assembly of active $K_{ATP}$ channels [3, 4]. SUR, a member of the ABC transporter family, originates from 2 separate genes and therefore occur in several spliced isoforms. SUR1 is found in the pancreatic β-cell and neurons [5], whereas SUR2A is in heart cells and SUR2B in smooth muscle [6]. Kir6.2 subunit forms the channel pore in the majority of tissues as pancreatic β-cell, brain, heart and skeletal muscle [3], while Kir6.1 can be found in smooth vascular muscle and astrocytes. These different channel forms have different pore properties and adenine nucleotide sensitivity [3] (FIG. 1). The KCNJ11 gene, encoding Kir6.2, and ABCC8 gene, encoding SUR1, are located at 11p15 [7], close to the large IDDM2 linkage peak.

Figure 2:
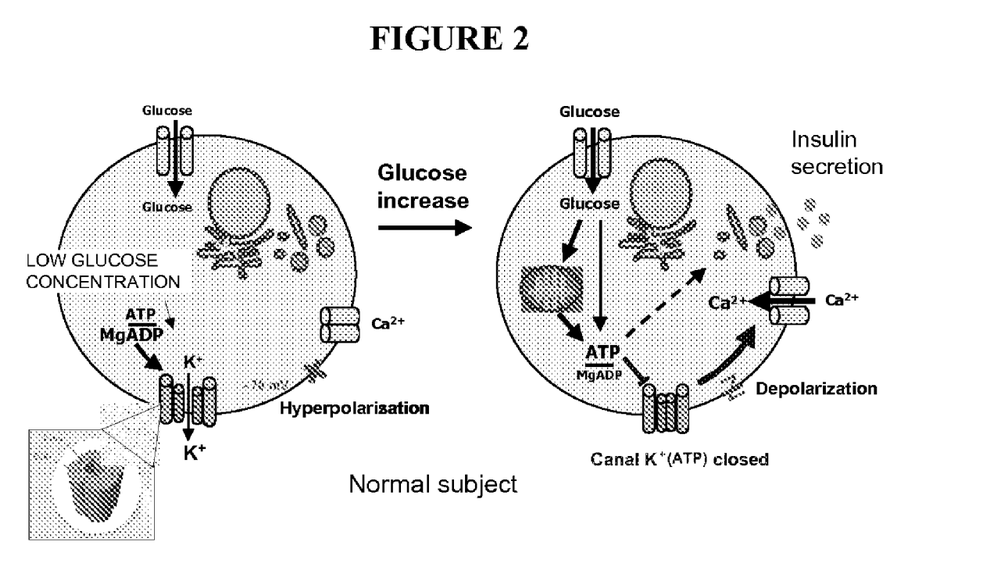
FIG. 2. $K_{ATP}$ channels coupling cell metabolism to electrical activity in pancreatic β-cell. In presence of low glucose and low ATP/ADP ratio, the $K_{ATP}$ channels are opened and the cell membrane hyperpolarized. When glucose concentration and therefore ATP/ADP ratio increase, the $K_{ATP}$ channels close, provoking membrane depolarisation, opening of the voltage-gated $Ca^{2+}$ channels and insulin exocytosis.

The $K_{ATP}$ channels play multiple physiological roles in the glucose metabolism regulation: insulin secretion by the pancreatic beta-cells, glucagon release by the pancreatic alpha-cells [8], somatostatin secretion from the D-cells [9], and GLP1 secretion from L cells [10]. When closed, the $K_{ATP}$ channel is said inactivated as the potassium efflux is blocked (but paradoxically this closure permits membrane depolarization and therefore the metabolic effect). Conversely, when opened, the channel is activated as the potassium efflux is effective. The sulfonylurea subunits sense changes in ATP and ADP concentration and thereby affect $K_{ATP}$ channel activity [11-13]. These nucleotides have opposite effects on the channel activity: ATP acts as a channel blocker and MgADP as a channel opener. In the pancreatic β-cell, at low glucose concentration, the potassium efflux through the opened $K_{ATP}$ channels ("activated") set up a membrane hyperpolarization (with potential about −70 mV). Increase in ATP concentration (and the concomitant decrease in MgAD) in response to the glucose metabolism closes the $K_{ATP}$ channels and is responsible for a membrane depolarization. This depolarization causes the opening of the voltage-gated $Ca^{2+}$ channels, allowing $Ca^{2+}$ entry triggering the exocytosis of insulin-containing granules [14] (FIG. 2). Furthermore, the $K_{ATP}$ channels are important for pancreatic insulin cell survival and regulates the differentiation of islet cells in the mice knock-out for Kir6.2 [15, 16].

In cardiac, smooth and skeletal muscle, brain neuron tissues, the $K_{ATP}$ channels are normally closed and open in response to metabolic stress and thereby leads to inhibition of electrical activity [17]. Furthermore, studies in Kir6.1 or Kir6.2 null mice show that $K_{ATP}$ channels are critical metabolic sensors in protection against metabolic stress as hyper or hypoglycemia, ischemia or hypoxia [18]. Cells expressing Kir6.2 mRNA are widely distributed throughout the brain [19] but the highest expression of $K_{ATP}$ channels is in the substantia nigra pars reticulata which plays a pivotal role in suppressing the propagation of generalized seizures [20, 21]. The opening of $K_{ATP}$ channels exerts a strong suppressive effect on neuronal activity during hypoxia by shifting membrane potentials in the hyperpolarized direction [22]. Mice lacking Kir6.2 are extremely susceptible to generalized seizure after brief hypoxia and $K_{ATP}$ channels might therefore participate in a preconditioning-induced neuronal protection mechanism [20, 21]. Neuroglycopenia stimulates the secretion of counter-regulatory hormones, among which the glucagon secretion by the pancreatic α-cells through activation of autonomic neurons. The $K_{ATP}$ channels have a major role for glucose sensing in ventro-medial hypothalamus neurons and is impaired in the Kir6.2 null mice leading to a markedly reduced glucagon secretion [23]. Besides, in behavioral tests, the Kir6.2 knock-out mice are less active, with impaired coordination and different emotional reactivity compared to the wild type, especially in novel situations [24].

In cardiac and skeletal muscle, the SUR2A isoform coexpressed with Kir6.2 is less sensitive to ATP [5]. The $K_{ATP}$ channel links energy status of muscle fibers to the electrical activity of cell membrane: they prevent the development of resting tension during fatigue and improve force recovery after fatigue [25]. Expressed in high density in the cardiac sarcolemma [5], $K_{ATP}$ channels are probably associated, as in the brain, with the cardioprotective mechanism ischemia-related preconditioning [26-29]. Under catecholamine surge, proper $K_{ATP}$ channel activity is required for normal membrane-dependant cellular functions, such as cellular loss of potassium and adequate calcium handling [26, 27, 29, 30]. A deficit in $K_{ATP}$ channel function in Kir6.2 null mice is recognized as a risk factor for arrhythmia under sympathetic stimulation [26, 31] and for greater susceptibility to ischemia under basal conditions [32]. However, the rapid heart rate of the mouse may magnify the relative importance of the $K_{ATP}$ channels compared to human. Nevertheless, mutations in the cardiac sulfonylurea receptor have been identified in patients with cardiomyopathy and ventricular arrhythmia [33]. In smooth vascular muscle, $K_{ATP}$ channels are involved in the vessel tone [34, 35]. Two kinds of mutations have been described in Kir6.2 or SUR1 subunits. First, inactivating mutations (as in hyperinsulinism) are responsible for permanent closure of the $K_{ATP}$ channels and therefore uncontrolled insulin exocytosis. Conversely, activating mutations (as in neonatal diabetes mellitus) provoke permanent opening of the channels and therefore membrane hyperpolarization and no insulin exocytosis.

Potassium Channel and Hyperinsulinism.

Persistent hyperinsulinemic hypoglycemia (HI) of infancy is a heterogeneous disorder which may be divided in two forms on the histopathological lesion (diffuse and focal) but which are clinically undistinguishable. Diffuse forms are characterized by an unregulated insulin secretion of the whole pancreas whereas focal forms correspond to somatic islet-cell hyperplasia [36-38]. Focal HI is sporadic and associated with hemi or homozygosity of a paternally inherited inactivating mutation of SUR1 or Kir6.2 and loss of the maternal allele in the hyperplasic islets [39, 40]. Diffuse HI is a heterogeneous disorder [41] which can he caused by various defects in the regulation of insulin secretion: inactivating Kir6.2 or SUR1 mutation, mutations of glucokinase [42], glutamate dehydrogenase [43, 44], short-chain L-3-hydroxyacyl-CoA dehydrogenase [45], and modifications in the insulin receptor [46]. Recessive homozygous or double heterozygous SUR1 or Kir6.2 mutations [47-51] are responsible for the majority of cases of diffuse and severe neonatal HI (80%) resistant to medical treatment and often require subtotal pancreatectomy. Dominant SUR1 and Kir6.2 mutations are responsible for reducing 50% of $K_{ATP}$ channel activity and causes less severe HI occurring during the first year of life and sensitive to diazoxide [52].

Detecting a Mutation in a Potassium Channel Gene or Polypeptide

Various techniques known in the art can be used to detect the presence of a particular mutation in a potassium channel gene (KCNJ11 or ABCC8) or polypeptide (Kir6.2 or SUR1). In particular, such techniques are typically performed in vitro or ex vivo, on a biological sample derived from the subject, such as a blood sample.

Examples of techniques known per se to the skilled person which may be used to determine the genotype include sequencing, any method employing amplification (e.g. PCR), specific primers, specific probes, migration, etc., typically quantitative RT-PCR, LCR (Ligase Chain Reaction), TMA (Transcription Mediated Amplification), PCE (an enzyme amplified immunoassay), DHPLC (Denaturing High Performance Liquid Chromatography), MLPA (Multiplex Ligation-dependent Probe Amplification) and bDNA (branched DNA signal amplification) assays.

In a particular embodiment, determining amino acid residue at any position in a polypeptide comprises a step of sequencing the channel gene or RNA or a portion thereof comprising the nucleotides encoding said amino acid residue.

In another particular embodiment, determining amino acid residue comprises a step of amplifying the gene or RNA or a portion thereof comprising the nucleotides encoding said amino acid residue. Amplification may be performed by polymerase chain reaction (PCR), such as simple PCR, RT-PCR or nested PCR, for instance, using conventional methods and primers.

In another particular embodiment, determining amino acid residue comprises a step of allele-specific restriction enzyme digestion. This can be done by using restriction enzymes that cleave the coding sequence of a particular allele and that do not cleave the other allele.

In a further particular embodiment, determining amino acid residue comprises a step of hybridization of the gene or RNA or a portion thereof comprising the nucleotides encoding said amino acid residue with a nucleic acid probe specific for the genotype, and determining the presence or absence of hybrids.

Kir6.2 Subunit of the Potassium Channel and Diabetes.

Figure 3:
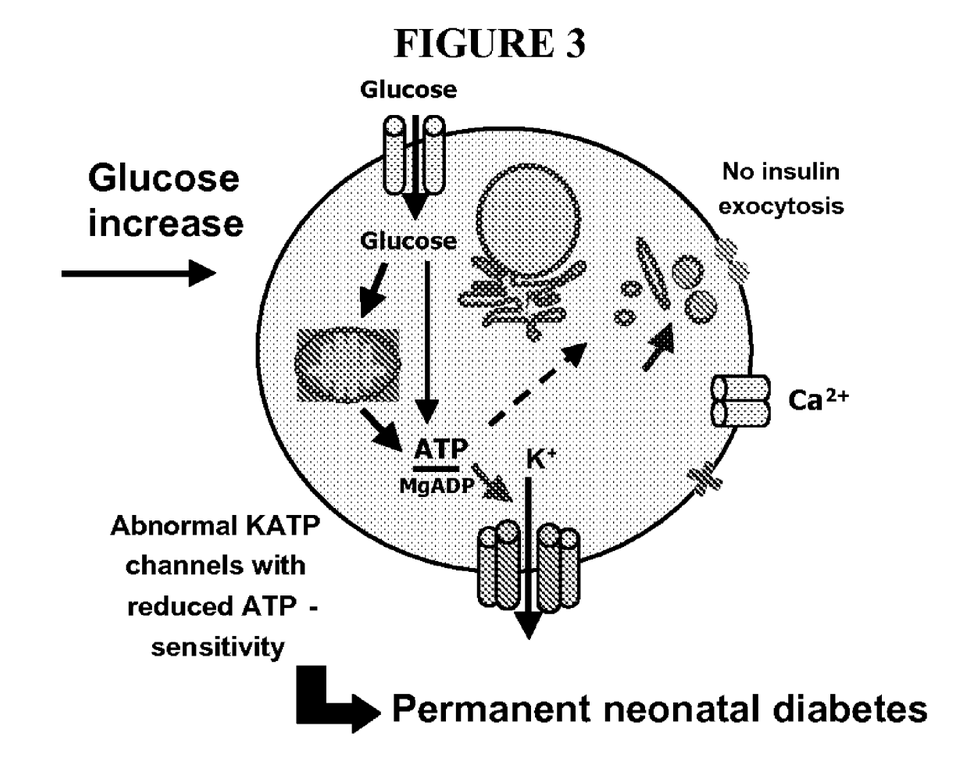
FIG. 3. Abnormal insulin secretion by KCNJ11 activating mutation. The activating mutation is responsible for reduced ATP-sensitivity of the channel and therefore the permanent opening of the channel inhibits the release of insulin when glucose increases.

Knowing the fundamental role of the $K_{ATP}$ channels in the insulin secretion and the Kir6.2 mutations implied in the hyperinsulinism of infancy, mutations in Kir6.2 encoded by KCNJ11 were searched for in type 1 and type 2 diabetes, assuming that $K_{ATP}$ channel overactivity could cause diabetes by inhibiting insulin secretion [53] (FIG. 3). Indeed, the common E23K polymorphism in Kir6.2 was found to be strongly associated to type 2 diabetes [54, 55], with decreased insulin secretion in glucose tolerance test [56] and diminished suppression of glucagon secretion in response to hyperglycemia [57]. Large population-based cohort of diabetics infant suggest that early-onset permanent diabetes settling before 6 months old differ from later onset cases by frequent "protective" HLA genotype for type 1 diabetes, less frequent autoimmunity and small-for-date birth weight [58].

Thus, several studies reported sequencing of KCNJ11, coding for Kir6.2, in patients with permanent neonatal diabetes mellitus without known etiology (mutations in glucokinase, insulin-promoter factor-1, PTF1a, FOXP3 and EIF2AK3 [59-63]) and found different mutations for 30 to 50% of the cases [14, 64, 65] (see Table 2). In our study of patients from the French Network for the Study of Neonatal Diabetes, we screened the KCNJ11 gene for 17 at-term babies with a median age at diagnosis of diabetes of 64 days (range 1-260). We identified in nine patients seven heterozygous mutations: 3 already described (V59M, R201H, R201C) and 4 novel mutations (F35L, G53N, E322K, Y330C). Most patients had a small birth weight, probably due to in utero insulin secretory insufficiency [64]. Mutations in KCNJ11 were also identified but with less frequency in transient neonatal diabetes cases [66]. Most of the mutations described (approximately 80% [14]) are de novo but one case has been reported with a demonstrated germline mosaicism suggesting that this possibility should be considered when counseling recurrence risk [67]. These mutations result in reduced ATP-sensitivity of the $K_{ATP}$ channels compared with the wild-types and the level of channel block is responsible for different clinical features: the "mild" form confers isolated permanent neonatal diabetes whereas the severe form combines diabetes and neurological symptoms such as epilepsy, developmental delay, muscle weakness and mild dysmorphic features [14, 64, 65, 68]. The most frequent mutations are located in the R201 (located on the C terminus) due to the presence of a CpG dinucleotide which is a hot spot mutation. Substitution on this amino acid by another positive charged residue has only small effects on ATP-sensitivity whereas the substitution with a neutral or negative charged amino acid causes major impairment in channel function [14, 69-71]. However, the decrease in ATP-sensitivity due to R201 mutation remains small and therefore is responsible for isolated neonatal diabetes whereas those causing greater reduction like V59M, V59G, Q52R are associated with severe disease [14, 64, 65, 68]. The 4 mutations identified [66, 72] in transient neonatal diabetes (R201H, G53S, G53R and I182V) result in milder reduction in ATP-sensitivity but the phenotype associated is variable as the mothers of the probands had permanent neonatal diabetes or diabetes revealed after 5 years old for 3 out of 4. The muscle weakness observed can be from both muscular and neurological origin as Kir6.2 is expressed in both cells. The developmental delay and the epilepsy results from the $K_{ATP}$ channels present in the central nervous system as described earlier. Conversely, no marked effect has been described on the heart function or the ECG and this may be explained by the greater ATP-inhibition of mutant Kir6.2/SUR2A than of Kir6.2/SUR1 [68, 73, 74].

Use of Sulfonylurea in Adults and Children with a KCNJ11 Mutation.

Sulfonylureas' effect on pancreatic β-cells has been discovered in 1942 by Janbon as patients treated for typhoid fever had severe hypoglycemia. Thereafter, sulfonylurea family developed rapidly and was used as treatment for diabetics not requiring insulin since 1956 [75]. Sulfonylureas close $K_{ATP}$ channels by binding with high affinity to SUR [74, 76, 77]. In the absence of added nucleotides, high-affinity inhibition of the $K_{ATP}$ current by sulfonylurea reaches only 60-80% [17].

SUR1 possesses two binding sites for glibenclamide whereas tolbutamide binds only to one [2, 74, 75]. This double binding may explain the glibenclamide long wash out time [78]. Besides binding the pancreatic $K_{ATP}$ channel, glibenclamide inhibits the activity of cardiac and skeletal or smooth muscle type channel [78] but also mitochondrial channels by binding to SUR2. Yet, this affinity of glibenclamide for SUR2 is 300 to 500 fold lower than to SUR1. Nevertheless, precautions may have to be taken when treating patients with ischemic heart disease at high dose of glibenclamide [78] as the $K_{ATP}$ channels intervene in the cardioprotective mechanism ischemia-related preconditioning as described above. However, the absence of side effects of this type reported in type 2 diabetes treatment suggests that the effects of extra pancreatic channel inhibition might be subtle.

The high affinity of sulfonylurea to the pancreatic $K_{ATP}$ channels suggested that these drugs may be used to replace insulin in these patients. Intravenous injection of tolbutamide could stimulate insulin secretion in patients with a KCNJ11 mutation even when they did not respond to intravenous glucose [14]. Subsequently, 6 patients have been successfully switched from insulin subcutaneous injections to oral sulfonylurea therapy [14, 79-81]. The dose of glibenclamide required have been up to 0.8 mg/kg/d, that is much higher doses than those used for type 2 diabetes treatment. The delay needed to stop insulin is between 3 days and 8 weeks with a follow up of nearly 2 years now. These results show great heterogeneity between the patients, even with the same KCNJ11 mutations. Our own experience shows a successful transfer from insulin to oral glibenclamide for 5 patients out of 7, the last two girls unable to transfer being twins with neurological features probably related to another pathology not yet understood, and for whom compliance was probably not optimal.

Our recent European collaborative study will report a total of 49 consecutive patients (from 3 months to 36 years old) from 40 families having a permanent neonatal diabetes by heterozygous mutation of KCNJ11 [82]. Of these 49 patients treated with adequate dose of sulfonylureas (0.8 mg/kg/day equivalent glibenclamide), 44 (90%) were able to stop insulin treatment. The median dose of glibenclamide initially required was 0.45 mg/kg/day (0.05 to 1.5 mg/kg/day). Glycemic control was improved in all 38 patients tested with a mean glycated hemoglobin level falling from 8.1% before sulfonylurea to 6.4% at 12 weeks after cessation of insulin, without enhancing the frequency of hypoglycaemia. Eighty percent (4 out of 5) of the patients unable to stop insulin had neurologic features in contrast with only 14% (6 out of 44) in the successful group. Five patients had transitory diarrhea, no other side effect was reported. Some studies have shown that closure of $K_{ATP}$ channels by sulfonylurea could induce β-cell apoptosis in human islets and therefore precipitate the decrease in the β-cell mass in type 2 diabetes patients but this responsibility must still be confirmed [83, 84]. However, concerning the patients with KCNJ11 mutations, even if the glibenclamide efficiency is transient for several years, it means years without daily subcutaneous injections and the subsequent improvement of quality of life (see personal testimony of a young boy after a successful switch to oral therapy in Diabetes UK Careline Journal, 2006). We therefore designed a protocol to transfer and evaluate children who have insulin treated diabetes due to KCNJ11 mutation, from insulin to sulfonylurea. We obtained the approval of the Clinical Research Direction of our institution (AP-HP, Paris France), as well as the agreement of the Ethical committee and of the French Authorities for Health Care (AFSSAPS), to include the children identified so far (n=12).

Transfer from Insulin to Glibenclamide: a Case Study

Figure 4:
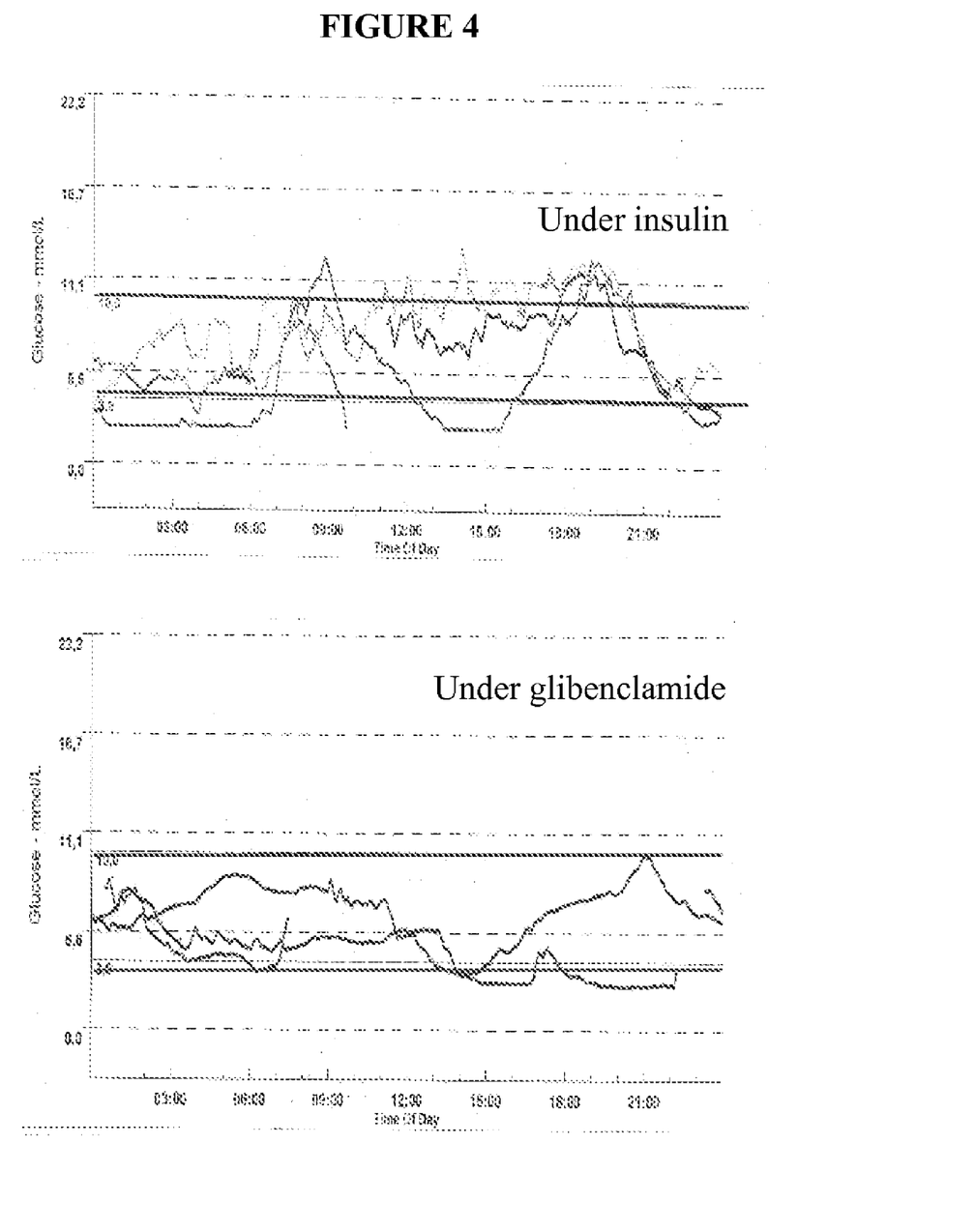
FIG. 4. Continuous monitoring of glycaemia during 3 days of a patient of 37 years old with R201H mutation, first under insulin and then under glibenclamide. See the decrease in the variability of the glycemic level after the transfer to glibenclamide.

We report here the case of a 37 years old patient with permanent neonatal diabetes discovered at 2 months old, during a systematic glucose monitoring as she was hospitalized for bilateral otitis. Metabolic control was fair under appropriate diet until she was 5 years when insulin therapy was initiated. However, despite many withdrawal of the injections for several days, she never had ketoacidosis. She had 2 children, the first one being a girl who revealed a permanent neonatal diabetes the first day of life and was immediately treated by insulin injections. The Kir6.2 mutation R201H was found in 2004 for both mother and daughter and we started glibenclamide therapy in January 2005. [82] The transfer was a great success as the first tablet taken was sufficient to stop permanently the insulin injections for both, with a required dose under 0.1 mg/kg/day of glibenclamide (mother at 36 years old, daughter at 15 years old). They both improved their glycemic control and their HbA1c (from 7.4% to 6% for the mother and from 9.5 to 7.9% for the daughter) with now 18 months follow up and no side effects, particularly no recurrent hypoglycemia. As shown in FIG. 4, the glycemic values were much more steady under glibenclamide than under insulin therapy.

SUR1, Diabetes Mellitus and Neuropsychological Features

Very recently, we observed seven heterozygous ABCC8 mutations in 9 of 34 patients with neonatal diabetes: L213R and I1424V in two persons with PND, and C435R, L582V, H1023Y, R1182Q or R1379C in persons with TND (Transient Neonatal Diabetes). The affected amino-acids are conserved in rat, mouse, the chicken, and the Japanese Fugu fish, suggesting that they are critical for channel function. We did not observe these mutations upon sequencing the relevant exons of 180 diabetic subjects and 140 unrelated non-diabetic white individuals of French origin. Furthermore, we detected no additional non-synonymous changes in the ABCC8 exons unaffected by mutations in a subset of 110 diabetic subjects, including 24 probands diagnosed with maturity onset diabetes of the young (MODY) from families without known MODY-associated mutations.

The partial pedigrees of families carrying the mutations has been carried out. The L213R, L582V (TND36), H1023Y, I1424V and R1379C (TND19) mutations are de novo mutations (the L582V, TND16, and R1397C, TND17, mutations were also inherited.) In the C435R, L582V (TND16), R1182Q and R1379C (TND17) families, the fathers were heterozygotes and the mutant alleles co-segregated with diabetes. The father of TND13 (C435R) was diagnosed with diabetes mellitus at age 13; after identification of his mutation, he discontinued insulin (after 24 years of treatment) upon successful response to glibenclamide (10 mg/day). An oral glucose tolerance test (OGTT) showed that the father of TND34 (R1182Q) has diabetes; he is currently being treated with diet alone. In the TND16 family, individuals II-3 and II-4 were diagnosed with diabetes after the age of 30 by OGTT and are currently treated with diet alone. At the age of 32, the father of TND17 (R1379C) developed diabetes, and is treated with glibenclamide. The R1379C allele was also identified in a grandmother, previously diagnosed with gestational diabetes and currently treated with diet, and a great aunt diagnosed with diabetes at age 44 and currently treated with sulfonylureas.

Therefore, we found ABCC8 mutations in 9 of the 34 ND cases in our case series in whom no genetic defect was previously identified. These 9 patients account for 12% of the 73 ND cases included in the study. Of the 29 PND patients in the study, 12 KCNJ11 cases account for 41%, 2 ABCC8 cases for 7%, while nearly 52% remain unexplained. Almost 57% of the 44 TND cases are attributable to chromosome 6q anomalies (n=25), 2% to KCNJ11 mutations (n=1) and ~15% to ABCC8 mutations (n=7). The etiology of eleven TND cases remains to be determined.

Diabetes

Table I provides a summary of the clinical characteristics of patients with mutant SUR1. Diabetes mellitus was diagnosed at a median age of 32 days (range: 3 to 125 days) with hyperglycemia leading to polyuria and polydipsia in 5 cases and ketoacidosis in 2 cases. TND 17 and 34 had low birth weights and hyperglycemia. There were no detectable anti-islet antibodies, and ultrasonography revealed no pancreatic abnormalities. Initial insulin treatment was required for 1, 2.5, 3, 4, 4, 8.5 and 10 months in probands TND16, 34, 17, 19, 13, 36, and 28, respectively. The last documented dose of insulin varied from 0.12 to 1.2 U/kg/day with a mean of 0.67 U/kg/day.

The SUR1 protein is the sulfonylurea receptor. Therefore the possibility that the mutation altered the binding and that no sulfonylurea binding could be present in the patient was considered. However and despite this theoretical possibility, following identification of their mutations, glibenclamide (glyburide) therapy was initiated and found to be successful in the PND patients: insulin was discontinued after 2 and 15 days in patients PND12 and 16, respectively. The current doses of glibenclamide (glyburide) are 0.59 and 0.22 mg/kg/day in patients PND12 and PND16, respectively. Two of the persons with TND required insulin again later in life. TND28 became hyperglycemic again at age 16, was treated with insulin and then shifted to glipizide (0.16 mg/kg/day). TND 19 required insulin at age 11 and at age 16 was switched to glibenclamide (0.28 mg/kg/day). These doses are at the high end of, or exceed, doses of glipizide and glibenclamide currently recommended by the United States FDA for treating type 2 diabetes in adults.

TABLE 1

Clinical Characteristics of Probands with Neonatal Diabetes with Mutant SURL*

| Family No. | Mutation | Sex | Birth wk of Gestation | Weight g (percentile) | At Diagnosis Age days | Weight g | Presentation | Glucose mmol/liter | At Metabolic Testing Age yr | Height cm (SD)† | Weight kg (percentile) | Insulin U/kg/day | Current Treatment |
|---|---|---|---|---|---|---|---|---|---|---|---|---|---|
| Permanent neonatal diabetes |
| 12 | L213R | Male | 41 | 3065 (22) | 125 | 5320 | Polyuria, polydipsia | 28.6 | 4.75 | 107.5 (0) | 17 (50) | 0.12 | Glb, 10 mg/day |
| 16 | I1424V | Male | 40 | 3080 (25) | 13 | 3360 | Ketoacidosis | 66 | 16.5 | 178 (+0.9) | 69 (85) | 0.88 | Glb, 15 mg/day |
| Transient neonatal diabetes |
| 13 | C435R | Male | 40 | 3040 (25) | 32 | 3575 | Polyuria, polydipsia | 44.5 | 4.75 | 108.8 (+0.5) | 17.5 (75) | | |
| 16 | L582V | Male | 40 | 3350 (50) | 15 | 3210 | Polyuria, polydipsia | 51.4 | 5.25 | 117 (+1.9) | 18.4 (50) | | |
| 17 | R1379C | Female | 40 | 2050 (<3) | 3 | 2100 | Hyperglycemia | 6.9 | 5.25 | 114.5 (+1.6) | 19.5 (82) | | |
| 19 | R1379C | Female | 40 | 2330 (<3) | 60 | 4900 | Polyuria, polydipsia | 22 | 15.7 | 158 (−0.8) | 54 (70) | 1.2 | Glb, 10 mg/day |
| 28 | H1023Y | Male | 40 | 3400 (55) | 21 | NA | Ketoacidosis | 37.8 | 16 | 180 (+1.2) | 59.5 (60) | 0.5 | Glp, 10 mg/day |
| 34 | R1182Q | Male | 34 | 1830 (8) | 4 | 1680 | Hyperglycemia | 13.6 | 2 | 82 (−1.5) | 10.3 (8) | | |
| 36 | L587V | Male | 40 | 3570 (67) | 74 | 6100 | Polyuria, polydipsia | 34 | 1.8 | 92 (+2) | 14 (90) | | |

*Glb denotes glyburide,
NA not available, and Glp glipizide. To convert values for glucose to milligrams perdeciliter, divide by 0.05551.
†Values in parentheses are the standard deviation from the norm.

Neurological Muscular and Neuropsychological Features

Patient PND12 presented with developmental delay but, in contrast with some individuals carrying a KCNJ11 mutation, did not have seizures or muscle weakness. His parents reported motor and developmental delay, which was subsequently documented to include dyspraxia. TND17 presented with minor dystonia. TND16 showed slow ideation and TND13 displayed minor visual-spatial dyspraxia. None had the facial features associated with some KCNJ11 mutations. None of the other index cases presented abnormal cognitive function or development.

ABCC8/SUR1 is expressed in the brain and therefore mutations of this gene may be directly responsible for the neurological features observed in some of the patients.

Metabolic Tests

The baseline fasting levels of C-peptide in patients PND12 and 16 were low (0.24 and 0.63 nM), but increased 358 and 222% to 1.1 and 1.4 nM, respectively, 2 hours after treatment with oral glibenclamide. Consistent with beta-cell dysfunction, stimulation by glucagon was impaired, with increments of 79% (0.19 nM) and 106% (0.67 nM) over baseline levels. (A normal response is an increment of at least 150%.)

Clinical Features of ND According to Genetic Etiology

The birth weights for TND cases linked to anomalies of chromosome 6 (TND-6q; n=25) were low, often in the lowest three percent of the population (20/25 vs 2/7, P=0.014), when compared with those of persons with TND caused by mutant SUR1 (Table I and Supplement). Macroglossia was present in 4 of 25 TND-6q24 probands, but not in the TND-SUR1 patients. Diabetes was diagnosed earlier in TND-6q24 compared to TND-SUR1 patients (mean of 4 days vs 29.9 days, P<0.05), which probably reflects, at least in part, the lower birth weights of the TND-6q24 patients (20 cases versus 2, respectively, P=0.019), rendering a greater likelihood of systematic glucose monitoring. Other clinical features did not differ, including developmental delay, the frequency and time of recurrence of diabetes. Chromosome 6 anomalies were not associated with PND.

Comparison of persons with ND caused by mutant SUR1 (n=9) with those with ND caused by mutant $K_{IR}6.2$ (n=13) showed no significant difference in distribution of low birth weight, age of diagnosis, or glucose levels at presentation. Ketoacidosis was more frequently associated with diabetes caused by mutant $K_{IR}6.2$ than diabetes caused by mutant SUR1 (9/13 vs 219), but this difference (P=0.09) was not statistically significant, possibly because of small sample size. The prevalence of developmental delay was not different (3/13 vs 1/9) and epilepsy was diagnosed in 1/13 ND-$K_{IR}6.2$ cases, but none of the ND-SUR1 cases. Dyspraxia was observed in two cases of ND-$K_{IR}6.2$ and one of ND-SUR1. In our case series, KCNJ11 mutations are mainly associated with PND (12/13), whereas the majority of ABCC8 mutations (7/9) are linked to TND.

Our results indicate that heterozygous, activating mutations in ABCC8, encoding the SUR1 regulatory subunit of the ATP-sensitive K$^+$ channels found in beta-cells, cause both permanent and transient neonatal diabetes. Comparison of the ND-SUR1 vs ND-$K_{IR}6.2$ patients revealed no significant differences in the prevalence of low birth weight, age of diagnosis, or severity of hyperglycemia or accompanying ketoacidosis. KCNJ11 mutations are typically associated with PND, while the majority of ABCC8 mutations are associated with TND, perhaps reflecting a less severe form of diabetes.

Previous reports have highlighted a heterogeneity of symptoms associated with ND caused by mutant $K_{IR}6.2$, which may reflect the sharing of the $K_{IR}6.2$ pore by both SUR1/$K_{IR}6.2$ neuroendocrine channels and sarcolemmal SUR2A/$K_{IR}6.2$ channels. The neurological features of several persons with ND-SUR1 imply that SUR1-containing $K_{ATP}$ channels can control the membrane potential of neuronal cells, such as inhibitory motor neurons.

The diagnosis of diabetes in the fathers with ABCC8 mutations is consistent with adult-onset type 2 diabetes or a mild form of TND. The systematic blood screening in French newborns makes the latter unlikely, and we propose that ABCC8 mutations may give rise to a novel monogenic form

TABLE S1

Comparison of Clinical Features* of ND Patients with Mutant KCNJ11, ABCC8 or Abnormal 6q24.

|  | PND-KCNJ11 (n = 12) | PND-ABCC8 (n = 2) | TND-ABCC8 (n = 7) | TND-6q24 (n = 25) |
|---|---|---|---|---|
| GESTATION |  |  |  |  |
| Weeks | 38.2 (38-41) | 40.5 (40-41) | 39.4 (34-40) | 35 (36-41) |
| Weight (g) | 2680.7 (2110-3260) < 3-60 | 3072 (3065-3080)22-25 | 2795 (1830-3570) < 3-67 | 1830 (1200-3570) < 3-26 |
| AT DIAGNOSIS |  |  |  |  |
| Age (day) | 67 (1-127) | 79 (33-125) | 29.9 (3-74) | 4 (1-34) |
| Weight (g) | 3581 (2110-5040) | 4340 (3360-5320) | 3594.2 (1680-6100) | 1894 (1200-6100) |
| Glucose (mmol/liter) | 37.5 (9.5-55) | 47.3 (28.5-58) | 34 (5.9-51.4) | 22 (7.3-43.6) |
| % of patients with |  |  |  |  |
| ketoacidosis | 75 | 50 | 14 | 4 |
| polyuria and polydipsis | 8 | 50 | 57 | 8 |
| glucose monitoring | 17 | 0 | 29 | 88 |
| Months of initial insulin therapy | Not applicable | Not applicable | 4 (1-10) | 2.8 (0-35) |
| % of patients with neurologic features |  |  |  |  |
| developmental delay | 25 | 50 | 0 | 12 |
| seizures or epilepsy | 8 | 0 | 0 | 0 |
| dyspraxia | 17 | 0 | 14 | 0 |

*averaged characteristics are expressed as mean(range)percentile.

of type 2 diabetes, with variable expression and age of onset. The potential contribution of overactive ABCC8 mutations to familial early onset type 2 diabetes remains to be evaluated, but the present report emphasizes how molecular understanding of a rare pediatric form of diabetes may illuminate the more common form of the disease.

In clinical practice there is no way to distinguish between patients with ABCC8 or KCNJ11 mutations vs abnormalities in chromosome 6q24. Gene sequencing is required, and a useful strategy is to screen chromosome 6 and the short intronless KCNJ11 first, unless the parents present with fasting hyperglycemia, in which case GCK is analyzed. If no mutations are identified, ABCC8 is analyzed. Genetic testing clearly has profound implications for the counseling and therapy for patients with ND. Indeed, unexpectedly in the presence of a mutation in their receptor, sulfonylureas proved effective in stopping the insulin treatment in the young and adult patients.

Neuropsychological Features, Kir6.2, SUR1 and Sulfonylurea Treatment

The following additional results that molecules that bind to the potassium channel (as sulfonylureas) may impact positively on the neurodevelopmental aspects of children bearing mutation in Kir6.2 subunit.

A 5 month-old girl was seen with infantile spasms, developmental delay, early onset diabetes. She had a heterozygous activating mutation in Kir6.2. Infantile spasms with hypsarrhythmia on the electroencephalogram were severe and refractory to steroids. Addition of oral sulfonylurea allowed a partial and transitory control of the epilepsy.

One subject who has a private KCNJ11 mutation developed mild developmental difficulties associated with permanent diabetes mellitus. Following sulfonylureas treatment, insulin could be stopped and neuropsychological milestones improved. Concentration ability, fine motor skills were reported by the parents to improve.

Furthermore, the rest of the patients (10 with either ABCC8 (Sur1) or KCNJ11 (KIR6.2)) showed improvement in neuropsychological functioning as a consequence of transfer to sulfonylureas. Obvious was that muscular tone was improved, as well as global behavioural features.

Based on those two cases and those observations, prospective clinical trial is under way, both in patients with Kir6.2 and SUR1 mutations to further substantiate the beneficial effects of sulfonylureas on neuropsychological development in those children with a mutation in the potassium channel. The drugs have been shown to cross the blood brain barrier.

Clinical Trial

The inventors initiated a clinical trial for switching children with permanent neonatal diabetes mellitus due to Kir6.2 activating mutation or SUR1 mutation for subcutaneous insulin to oral glibenclamide therapy.

This trial included 10 patients. The purpose of this trial is firstly therapeutic by switching the patients from subcutaneous insulin to oral glibenclamide therapy and cognitive by evaluating the potential improvement under glibenclamide therapy of the neurological and developmental status of the patients. One patient has been excluded from the trial. The patients received an increasing amount of gibenclamide from 0.3 mg/kg/day the first day until 0.8 mg/kg/day or the dose allowing to stop the insulin treatment and to obtain a correct glycaemia. The dose is administered in 2, 3 or 4 times depending on the eating habit.

A neurological and developmental status is established just before the switch and two, six, twelve and eighteen months after the beginning of the gibenclamide treatment.

Each patient has been submitted to a fine neurodevelopmental evaluation, in particular according to the scales assessing in a quantitative manner the neuropsychomotor development in children (www.ecpa.fr/default site.asp?idx33). More specifically, neuropsychomotor testing included the studies of the tonus, lateralization, motor coordination (static and dynamic), praxies and gnosies, attention capacities, spatial abilities (battery of tests: NP-MOT, ECPA-Elsevier Editor, Vaivre-Douret, 2006 and EMG test, ECPA editor, Vaivre-Douret, 1997). For young children (0 to 4 years of age) scale of motor development was used (DF-MOT, ECPA editor, Vaivre-Douret, 1999) as well as global and fine motor skills, giving an age of motor development. Neuropsychological testing included: oculo-motor skills, first then writing (BHK test, ECPA), skills for time (Stambak), different memory skills, visual abilities (de Rey test), visual-motor coordination (Beery test), visuo-spatial skills (Khos test, Rey image), executive skills (Porteus labyrinthe and/or London tower test of the NEPSY), visuo-spatial attention ability, writing speed and language abilities.

For the opthalmologic evaluation, several criteria are determined. For children of less than 6, scotopic and photopic electroretinogram (ERG) and visual evoked potentials (PEV) are determined. For children of more than 6, cone ERG, Single Flash ERG, PEV and sensorial electro-oculography are performed.

Hypotonia has only be stated in patients having a Kir6.2 mutation.

8 of the 9 patients have a successful switching treatment for diabetes.

3 of the 9 patients have been evaluated after switching treatment and all of them showed a clear opthalmologic or neuropsychologic improvement.

In particular, a boy being 15 months-old and having a Kir6.2 mutation showed lengthened VEP (visual evoked potentials) (>150 ms). After 6 months of switching treatment, he showed a clear improvement for VEP of 20 ms.

Another boy being 5 months-old and having a Kir6.2 mutation showed a hypotonia of the axis, and a significant development delay of 1 month. After 6 months of switching treatment, he showed no more hypotonia of the axis and no more development delay. Therefore, this patient demonstrates an improvement of tonus and development.

Finally, a boy having a L213R SUR1 mutation and being seven-years old showed after 18 months of switched treatment a better planification, an improvement of the attention disorder, a language improvement and a decrease of the anguish.

General Conclusions

In conclusion, the $K_{ATP}$ channels have a central role in cell response to metabolic changes in many organs and especially in pancreatic β-cell. The advances in the comprehension of the physiological function of these channels, and in particular of the Kir6.2 and SUR1 subunits, has found a major clinical application for patients having permanent and recurrent neonatal diabetes or late onset diabetes due to a KCNJ11 and ABCC8 mutations. The transfer from insulin injections to oral glibenclamide therapy is highly effective for most patients and safe.

This illuminates how the molecular understanding of some monogenic form of diabetes may lead to an unexpected change of the treatment in children. This is a spectacular example by which a pharmacogenomic approach improves in a tremendous way the quality of life of our young patients.

TABLE 2

Mutations of KCNJ11 gene identified in permanent neonatal diabetes and phenotypical features associated

| Mutation | Sex | Age of diabetes | Clinical features | Reference |
|---|---|---|---|---|
| R201C De novo | M | 37 days | Normal | Vaxillaire et al Diabetes 53: 2719-2722, 2004 |
| R201H De novo | M | 17 days | Normal | |
| V59M De novo | M | 127 days | Leucodystrophy Developmental delay Oesophagia | |
| E322K De novo | F | 3 days | Normal | |
| R201C De novo | F | 1.25 months | Normal | Edghill et al Diabetes 53: 2998-3001, 2004 |
| R176C Sisters and mother with mutation but no diabetes | F | 17 months | Normal | |
| R201H Son underneath | F | 6 weeks | Normal | Gloyn et al [14] |
| R201H | M | Birth | Normal | |
| R201H | F | 6 weeks | Normal | |
| R201C | M | 4 weeks | Normal | |
| R201H | F | 15 weeks | Normal | |
| V59M | M | Birth | Normal | |
| R201H Father of 2 underneath | M | 12 weeks | Normal | |
| R201H | M | <4 weeks | Normal | |
| R201H | M | <3 weeks | Normal | |
| V59M | M | 5 weeks | Muscle weakness Developmental delay | |
| V59G | M | 1 week | Muscle weakness Developmental delay Epilepsy Dysmorphic features | |
| Q52R | M | 5 weeks | Muscle weakness Developmental delay Epilepsy Dysmorphic features | |
| I296L | F | 26 weeks | Muscle weakness Developmental delay Epilepsy Dysmorphic features | |
| R201H | M | 68 days | Normal | Zung et al [73] |
| F35V | | 12 weeks | Normal | Sagen et al [74] |
| V59M | | 1 week | Neurological features | |
| V59M | | 6 weeks | Neurological features | |
| V59M | | 6 weeks | Neurological features | |
| R201H Mother of underneath | F | 24 weeks | Normal | |
| R201H | | 2 weeks | Normal | |
| Y330C Father of underneath | M | <1 week | Neurological features | |
| Y330C | | 6 weeks | Normal | |
| F333I | | 10 weeks | Normal | |
| R201H | M | 3 weeks | Normal | Klupa et al Diabetologia 48: 1029-31 2005 |
| R201L | F | 4.1 months | | Codner et al [75] |
| V59M | M | 3 days | | Massa et al [65] |
| K170R | M | 40 days | | |
| R201C | M | 49 days | Muscle weakness Developmental delay | |
| V59M | M | 58 days | Developmental delay | |
| V59M | F | 60 days | Muscle weakness Developmental delay | |
| K170N | F | 63 days | Developmental delay | |
| R50P | M | 87 days | Developmental delay | |
| V59M | M | 182 days | | |
| C42R | M | 6 weeks to 12 months | Normal | Yorifuji et al JCEM 90: 3174-78 2005 |

TABLE 2-continued

Mutations of KCNJ11 gene identified in permanent neonatal diabetes and phenotypical features associated

| Mutation | Sex | Age of diabetes | Clinical features | Reference |
| --- | --- | --- | --- | --- |
| C42R Father of proband | M | 22 years | Normal | |
| C42R Grandfather of proband | M | 3 years Sulfonylurea at 23 years | Normal | |
| C42R Paternal aunt of proband | F | 28 years Sulfonylurea after 4 months | Normal | |
| H46Y, R50Q, G53D, L164P, C166Y, K170T, Y330S | | | | Flanagan et al Diabetologia 49: 1190-97 2006 |
| F35L | | | | Proks et al Diabetes 55: 1731-1737 2006 |
| R50Q | | | Normal | Shimomura et al Diabetes 55: 1705-12 2006 |
| C166F | F | 3 months | Developmental delay Severe epilepsy Hypotonia | Bahi-buisson et al Am J Hum Genet Suppl 1: 323 2004 |

TABLE 3

List of potassium channels ligands (including the sulfonylureas) available in France, (Source Vidal)

Hypoglycemic Sulfamides

Carbutamide = Glucidoral
Glibenclamide (glyburide USA) = Daonil et Daonil faible, Euglucan, Hemi-Daonil, Miglucan
Glibornuride = Glutril
Glicazide = Diamicron
Glimépiride = Amarel
Glipizide = Glibénèse, Minidiab, Ozidia Glinides (bind the potatium channel)

Répaglinide = NovoNorm

Associations

Metformine + glibenclamide = Glucovance

REFERENCES

1. Bryan, J., et al., Insulin secretagogues, sulfonylurea receptors and K(ATP) channels. Curr Pharm Des, 2005. 11 (21): p. 2699-716.
2. Mikhailov, M. V., et al., 3-D structural and functional characterization of the purified KATP channel complex Kir6.2-SUR1. Embo J, 2005. 24(23): p. 4166-75.
3. Bond, C. T., et al., Cloning and functional expression of the cDNA encoding an inwardly-rectifying potassium channel expressed in pancreatic beta-cells and in the brain. FEBS Lett, 1995. 367(1): p. 61-6.
4. Clement, J. P. t., et al., Association and stoichiometry of K(ATP) channel subunits. Neuron, 1997. 18(5): p. 827-38.
5. Inagaki, N., et al., A family of sulfonylurea receptors determines the pharmacological properties of ATP-sensitive K+ channels. Neuron, 1996. 16(5):p. 1011-7.
6. Isomoto, S., et al., A novel sulfonylurea receptor forms with BIR (Kir6.2) a smooth muscle type ATP-sensitive K+ channel. J Biol Chem, 1996. 271(40) p. 24321-4.
7. Inagaki, N., et al., Reconstitution of IKATP: an inward rectifier subunit plus the sulfonylurea receptor. Science, 1995. 270(5239): p. 1166-70.
8. Gopel, S. O., et al., Regulation of glucagon release in mouse-cells by KATP channels and inactivation of TTX-sensitive Na+ channels. J Physiol, 2000. 528(Pt 3): p. 509-20.
9. Gopel, S. O., et al., Patch-clamp characterisation of somatostatin-secreting-cells in intact mouse pancreatic islets. J Physiol, 2000. 528(Pt 3): p. 497-507.
10. Gribble, F. M., et al., A novel glucose-sensing mechanism contributing to glucagon-like peptide-1 secretion from the GLUTag cell line. Diabetes, 2003. 52(5): p. 1147-54.
11. Cook, D. L., et al., ATP-sensitive K+ channels in pancreatic beta-cells. Spare-channel hypothesis. Diabetes, 1988. 37(5): p. 495-8.
12. Aguilar-Bryan, L., et al., Cloning of the beta cell high-affinity sulfonylurea receptor: a regulator of insulin secretion. Science, 1995. 268(5209): p. 423-6.
13. Gribble, F. M., et al., Properties of cloned ATP-sensitive K+ currents expressed in Xenopus oocytes. J Physiol, 1997. 498 (Pt 1): p. 87-98.
14. Gloyn, A. L., et al., Activating mutations in the gene encoding the ATP-sensitive potassium-channel subunit Kir6.2 and permanent neonatal diabetes. N Engl J Med, 2004. 350(18): p. 1838-49.
15. Winarto, A., et al., Morphological changes in pancreatic islets of KATP channel-deficient mice: the involvement of KATP channels in the survival of insulin cells and the maintenance of islet architecture. Arch Histol Cytol, 2001. 64(1): p. 59-67.
16. Miki, T., et al., Roles of ATP-sensitive K+ channels in cell survival and differentiation in the endocrine pancreas. Diabetes, 2001. 50 Suppl 1: p. S48-51.
17. Proks, P., et al., Sulfonylurea stimulation of insulin secretion. Diabetes, 2002. 51 Suppl 3: p. S368-76.
18. Seino, S. and T. Miki, Gene targeting approach to clarification of ion channel function: studies of Kir6.x null mice. J Physiol, 2004. 554(Pt 2): p. 295-300.
19. Dunn-Meynell, A. A., N. E. Rawson, and B. E. Levin, Distribution and phenotype of neurons containing the ATP-sensitive K+ channel in rat brain. Brain Res, 1998. 814(1-2): p. 41-54.
20. Yamada, K. and N. Inagaki, Neuroprotection by KATP channels. J Mol Cell Cardiol, 2005. 38(6): p. 945-9.
21. Heron-Milhavet, L., et al., Protection against hypoxic-ischemic injury in transgenic mice overexpressing Kir6.2 channel pore in forebrain. Mol Cell Neurosci, 2004. 25(4): p. 585-93.
22. Yamada, K. and N. Inagaki, ATP-sensitive K(+) channels in the brain: sensors of hypoxic conditions. News Physiol Sci, 2002. 17: p. 127-30.

23. Miki, T., et al., ATP-sensitive K+ channels in the hypothalamus are essential for the maintenance of glucose homeostasis. Nat Neurosci, 2001. 4(5): p. 507-12.
24. Deacon, R. M., et al., Behavioral phenotyping of mice lacking the K ATP channel subunit Kir6.2. Physiol Behav, 2006. 87(4): p. 723-33.
25. Gong, B., et al., KATP channels depress force by reducing action potential amplitude in mouse EDL and soleus muscle. Am J Physiol Cell Physiol, 2003. 285(6): p. C1464-74.
26. Zingman, L. V., et al., Kir6.2 is required for adaptation to stress. Proc Natl Acad Sci USA, 2002. 99(20): p. 13278-83.
27. Hodgson, D. M., et al., Cellular remodeling in heart failure disrupts K(ATP) channel-dependent stress tolerance. Embo J, 2003. 22(8): p. 1732-42.
28. Kane, G. C., et al., ATP-sensitive K+ channel knockout compromises the metabolic benefit of exercise training, resulting in cardiac deficits. Diabetes, 2004. 53 Suppl 3: p. S169-75.
29. Terzic, A., A. Jahangir, and Y. Kurachi, Cardiac ATP-sensitive K+ channels: regulation by intracellular nucleotides and K+ channel-opening drugs. Am J Physiol, 1995. 269(3 Pt 1): p. C525-45.
30. Nichols, C. G. and W. J. Lederer, Adenosine triphosphate-sensitive potassium channels in the cardiovascular system. Am J Physiol, 1991. 261(6 Pt 2): p. H1675-86.
31. Liu, X. K., et al., Genetic disruption of Kir6.2, the pore-forming subunit of ATP-sensitive K+ channel, predisposes to catecholamine-induced ventricular dysrhythmia. Diabetes, 2004. 53 Suppl 3: p. S165-8.
32. Suzuki, M., et al., Role of sarcolemmal K(ATP) channels in cardioprotection against ischemia/reperfusion injury in mice. J Clin Invest, 2002. 109(4): p. 509-16.
33. Bienengraeber, M., et al., ABCC9 mutations identified in human dilated cardiomyopathy disrupt catalytic $K_{ATP}$ channel gating. Nat Genet, 2004. 36(4): p. 382-7.
34. Quayle, J. M., M. T. Nelson, and N. B. Standen, ATP-sensitive and inwardly rectifying potassium channels in smooth muscle. Physiol Rev, 1997. 77(4): p. 1165-232.
35. Kleppisch, T. and M. T. Nelson, ATP-sensitive K+ currents in cerebral arterial smooth muscle: pharmacological and hormonal modulation. Am J Physiol, 1995. 269(5 Pt 2): p. H1634-40.
36. Rahier, J., et al., The basic structural lesion of persistent neonatal hypoglycaemia with hyperinsulinism: deficiency of pancreatic D cells or hyperactivity of B cells? Diabetologia, 1984. 26(4): p. 282-9.
37. Rahier, J., et al., Partial or near-total pancreatectomy for persistent neonatal hyperinsulinaemic hypoglycaemia: the pathologist's role. Histopathology, 1998. 32(1): p. 15-9.
38. Sempoux, C., et al., Neonatal hyperinsulinemic hypoglycemia: heterogeneity of the syndrome and keys for differential diagnosis. J Clin Endocrinol Metab, 1998. 83(5): p. 1455-61.
39. de Lonlay, P., et al., Somatic deletion of the imprinted 11p15 region in sporadic persistent hyperinsulinemic hypoglycemia of infancy is specific of focal adenomatous hyperplasia and endorses partial pancreatectomy. J Clin Invest, 1997. 100(4): p. 802-7.
40. Verkarre, V., et al., Paternal mutation of the sulfonylurea receptor (SUR1) gene and maternal loss of 11p15 imprinted genes lead to persistent hyperinsulinism in focal adenomatous hyperplasia. J Clin Invest, 1998. 102(7): p. 1286-91.
41. Dunne, M. J., et al., Hyperinsulinism in infancy: from basic science to clinical disease. Physiol Rev, 2004. 84(1): p. 239-75.
42. Glaser, B., et al., Familial hyperinsulinism caused by an activating glucokinase mutation. N Engl J Med, 1998. 338(4): p. 226-30.
43. Stanley, C. A., et al., Hyperinsulinism and hyperammonemia in infants with regulatory mutations of the glutamate dehydrogenase gene. N Engl J Med, 1998. 338(19): p. 1352-7.
44. Zammarchi, E., et al., Biochemical evaluation of a patient with a familial form of leucine-sensitive hypoglycemia and concomitant hyperammonemia. Metabolism, 1996. 45(8): p. 957-60.
45. Clayton, P. T., et al., Hyperinsulinism in short-chain L-3-hydroxyacyl-CoA dehydrogenase deficiency reveals the importance of beta-oxidation in insulin secretion. J Clin Invest, 2001. 108(3): p. 457-65.
46. Hojlund, K., et al., A novel syndrome of autosomal-dominant hyperinsulinemic hypoglycemia linked to a mutation in the human insulin receptor gene. Diabetes, 2004. 53(6): p. 1592-8.
47. Thomas, P. M., et al., Mutations in the sulfonylurea receptor gene in familial persistent hyperinsulinemic hypoglycemia of infancy. Science, 1995. 268(5209): p. 426-9.
48. Thomas, P., Y. Ye, and E. Lightner, Mutation of the pancreatic islet inward rectifier Kir6.2 also leads to familial persistent hyperinsulinemic hypoglycemia of infancy. Hum Mol Genet, 1996. 5(11): p. 1809-12.
49. Kane, C., et al., Loss of functional $K_{ATP}$ channels in pancreatic beta-cells causes persistent hyperinsulinemic hypoglycemia of infancy. Nat Med, 1996. 2(12): p. 1344-7.
50. Nestorowicz, A., et al., Mutations in the sulonylurea receptor gene are associated with familial hyperinsulinism in Ashkenazi Jews. Hum Mol Genet, 1996. 5(11): p. 1813-22.
51. Nestorowicz, A., et al., A nonsense mutation in the inward rectifier potassium channel gene, Kir6.2, is associated with familial hyperinsulinism. Diabetes, 1997. 46(11): p. 1743-8.
52. Huopio, H., et al., A new subtype of autosomal dominant diabetes attributable to a mutation in the gene for sulfonylurea receptor 1. Lancet, 2003. 361 (9354) p. 301-7.
53. Koster, J. C., et al., Targeted overactivity of beta cell K(ATP) channels induces profound neonatal diabetes. Cell, 2000. 100(6): p. 645-54.
54. Hani, E. H., et al., A missense mutation in hepatocyte nuclear factor-4 alpha, resulting in a reduced transactivation activity, in human late-onset non-insulin-dependent diabetes mellitus. J Clin Invest, 1998. 101(3): p. 521-6.
55. Gloyn, A. L., et al., Large-scale association studies of variants in genes encoding the pancreatic beta-cell $K_{ATP}$ channel subunits Kir6.2 (KCNJ11) and SUR1 (ABCC8) confirm that the KCNJ11 E23K variant is associated with type 2 diabetes. Diabetes, 2003. 52(2): p. 568-72.
56. Florez, J. C., et al., Haplotype structure and genotype-phenotype correlations of the sulfonylurea receptor and the islet ATP-sensitive potassium channel gene region. Diabetes, 2004. 53(5): p. 1360-8.
57. Tschritter, O., et al., The prevalent Glu23Lys polymorphism in the potassium inward rectifier 6.2 (KIR6.2) gene is associated with impaired glucagon suppression in response to hyperglycemia. Diabetes, 2002. 51(9): p. 2854-60.
58. Iafusco, D., et al., Permanent diabetes mellitus in the first year of life. Diabetologia, 2002. 45(6): p. 798-804.
59. Polak, M. and J. Shield, Neonatal and very-early-onset diabetes mellitus. Semin Neonatol, 2004. 9(1): p. 59-65.

60. Metz, C., et al., Neonatal diabetes mellitus: chromosomal analysis in transient and permanent cases. J Pediatr, 2002. 141(4): p. 483-9.
61. Njolstad, P. R., et al., Neonatal diabetes mellitus due to complete glucokinase deficiency. N Engl J Med, 2001. 344(21): p. 1588-92.
62. Njolstad, P. R., et al., Permanent neonatal diabetes caused by glucokinase deficiency: inborn error of the glucose-insulin signaling pathway. Diabetes, 2003. 52(11): p. 2854-60.
63. Edghill, E. L., et al., Activating mutations in the KCNJ11 gene encoding the ATP-sensitive K+ channel subunit Kir6.2 are rare in clinically defined type 1 diabetes diagnosed before 2 years. Diabetes, 2004. 53(11): p. 2998-3001.
64. Vaxillaire, M., et al., Kir6.2 mutations are a common cause of permanent neonatal diabetes in a large cohort of French patients. Diabetes, 2004. 53(10): p. 2719-22.
65. Massa, O., et al., KCNJ11 activating mutations in Italian patients with permanent neonatal diabetes. Hum Mutat, 2005. 25(1): p. 22-7.
66. Gloyn, A. L., et al., Relapsing diabetes can result from moderately activating mutations in KCNJ11. Hum Mol Genet, 2005. 14(7): p. 925-34.
67. Proks, P., et al., Molecular basis of Kir6.2 mutations associated with neonatal diabetes or neonatal diabetes plus neurological features. Proc Natl Acad Sci USA, 2004. 101 (50): p. 17539-44.
68. Antcliff, J. F., et al., Functional analysis of a structural model of the ATP-binding site of the $K_{ATP}$ channel Kir6.2 subunit. Embo J, 2005. 24(2): p. 229-39.
69. John, S. A., et al., Molecular mechanism for ATP-dependent closure of the K+ channel Kir6.2. J Physiol, 2003. 552(Pt 1): p. 23-34.
70. Ribalet, B., S. A. John, and J. N. Weiss, Molecular basis for Kir6.2 channel inhibition by adenine nucleotides. Biophys J, 2003. 84(1): p. 266-76.
71. Tammaro, P., P. Proks, and F. M. Ashcroft, Functional effects of naturally occurring KCNJ11 mutations causing neonatal diabetes on cloned cardiac KATP channels. J Physiol, 2006. 571(Pt 1): p. 3-14.
72. Gribble, F. M., et al., Tissue specificity of sulfonylureas: studies on cloned cardiac and beta-cell K(ATP) channels. Diabetes, 1998. 47(9): p. 1412-8.
73. Zung, A., et al., Glibenclamide treatment in permanent neonatal diabetes mellitus due to an activating mutation in Kir6.2. J Clin Endocrinol Metab, 2004. 89(11): p. 5504-7.
74. Sagen, J. V., et al., Permanent neonatal diabetes due to mutations in KCNJ11 encoding Kir6.2: patient characteristics and initial response to sulfonylurea therapy. Diabetes, 2004. 53(10): p. 2713-8.
75. Codner, E., et al., High-dose glibenclamide can replace insulin therapy despite transitory diarrhea in early-onset diabetes caused by a novel R201L Kir6.2 mutation. Diabetes Care, 2005. 28(3): p. 758-9.
76. Henquin, J. C., Pathways in beta-cell stimulus-secretion coupling as targets for therapeutic insulin secretagogues. Diabetes, 2004. 53 Suppl 3: p. S48-58.
77. Gribble, F. M. and F. M. Ashcroft, Differential sensitivity of beta-cell and extrapancreatic K(ATP) channels to gliclazide. Diabetologia, 1999. 42(7) p. 845-8.
78. Gribble, F. M., S. J. Tucker, and F. M. Ashcroft, The interaction of nucleotides with the tolbutamide block of cloned ATP-sensitive K+ channel currents expressed in Xenopus oocytes: a reinterpretation. J Physiol, 1997. 504 (Pt 1): p. 35-45.
79. Nagashima, K., et al., Sulfonylurea and non-sulfonylurea hypoglycemic agents: pharmachological properties and tissue selectivity. Diabetes Res Clin Pract, 2004. 66 Suppl 1: p. S75-8.
80. Maedler, K., et al., Sulfonylurea induced beta-cell apoptosis in cultured human islets. J Clin Endocrinol Metab, 2005. 90(1): p. 501-6.
81. Rustenbeck, I., et al., Beta-cell toxicity of ATP-sensitive K+ channel-blocking insulin secretagogues. Biochem Pharmacol, 2004. 67(9): p. 1733-41.
82. Pearson et al, Switching from Insulin to Oral sulfonylureas in patients with diabetes due to Kir6.2 mutations, New England Journal of Medicine, in Publication.

The invention claimed is:

1. A method of treating diabetes mellitus comprising administering an effective amount of a composition comprising an ATP-sensitive potassium channel ligand to a subject having a defective, mutated potassium channel SUR1 subunit in need of treatment for diabetes mellitus, wherein the mutated SUR1 polypeptide exhibits at least one of the following amino acid mutations: L213R, I1424V, C435R, L582V, H1023Y, R1182Q or R1379C, and wherein the ATP-sensitive potassium channel ligand is selected from the group consisting of glibenclamide (glyburide), carbutamide, glibornuride, glicazide, glimepiride, glipizide and combinations thereof.

2. The method of claim 1, wherein said ATP-sensitive potassium channel ligand is glibenclamide (glyburide).

3. The method of claim 1, wherein said ATP-sensitive potassium channel ligand is carbutamide.

4. The method of claim 1, wherein said ATP-sensitive potassium channel ligand is glibornuride.

5. The method of claim 1, wherein said ATP-sensitive potassium channel ligand is glicazide.

6. The method of claim 1, wherein said ATP-sensitive potassium channel ligand is glimepiride.

7. The method of claim 1, wherein said ATP-sensitive potassium channel ligand is glipizide.

8. The method of claim 1, wherein said composition comprises a combination of said ATP-sensitive potassium channel ligands.

* * * * *

UNITED STATES PATENT AND TRADEMARK OFFICE
CERTIFICATE OF CORRECTION

PATENT NO. : 8,354,452 B2
APPLICATION NO. : 12/373982
DATED : January 15, 2013
INVENTOR(S) : Michael Polak and Paul Czernichow Page 1 of 1

It is certified that error appears in the above-identified patent and that said Letters Patent is hereby corrected as shown below:

In the Specification

Column 4,
Line 36, "mefformine" should read --metformine--.

Column 14,
Line 7, "(9/13 vs 219)" should read --(9/13 vs 2/9)--.

Signed and Sealed this
Twenty-sixth Day of November, 2013

Margaret A. Focarino
*Commissioner for Patents of the United States Patent and Trademark Office*